United States Patent
Miwa et al.

(10) Patent No.: US 12,207,880 B2
(45) Date of Patent: Jan. 28, 2025

(54) ULTRASONIC TONOMETER

(71) Applicant: NIDEK CO., LTD., Aichi (JP)

(72) Inventors: Tetsuyuki Miwa, Aichi (JP); Tsutomu Uemura, Aichi (JP); Kazunari Shimizu, Aichi (JP)

(73) Assignee: NIDEK CO., LTD., Aichi (JP)

( * ) Notice: Subject to any disclaimer, the term of this patent is extended or adjusted under 35 U.S.C. 154(b) by 948 days.

(21) Appl. No.: 17/255,036

(22) PCT Filed: Jul. 2, 2019

(86) PCT No.: PCT/JP2019/026391
§ 371 (c)(1),
(2) Date: Dec. 22, 2020

(87) PCT Pub. No.: WO2020/009130
PCT Pub. Date: Jan. 9, 2020

(65) Prior Publication Data
US 2021/0259548 A1  Aug. 26, 2021

(30) Foreign Application Priority Data

| Jul. 2, 2018 | (JP) | 2018-126415 |
| Jul. 2, 2018 | (JP) | 2018-126416 |
| Aug. 1, 2018 | (JP) | 2018-145482 |

(51) Int. Cl.
*A61B 3/16* (2006.01)
*A61B 3/00* (2006.01)

(52) U.S. Cl.
CPC ............ *A61B 3/165* (2013.01); *A61B 3/0041* (2013.01)

(58) Field of Classification Search
CPC ....... A61B 3/16; A61B 5/0002; A61B 5/4839; A61B 5/6814; A61B 8/06; A61B 3/165;
(Continued)

(56) References Cited

U.S. PATENT DOCUMENTS

| 5,396,888 A | 3/1995 | Massie et al. |
| 2002/0082056 A1 | 6/2002 | Mandai et al. |

(Continued)

FOREIGN PATENT DOCUMENTS

| JP | H05-253190 A | 10/1993 |
| JP | 2002-192074 A | 7/2002 |

(Continued)

OTHER PUBLICATIONS

International Search Report (ISR) dated Sep. 17, 2019 filed in PCT/JP2019/026391.

*Primary Examiner* — Brandi N Thomas
(74) *Attorney, Agent, or Firm* — RANKIN, HILL & CLARK LLP

(57) ABSTRACT

An ultrasonic tonometer for measuring the eye pressure of an examinee's eye by means of an ultrasonic wave includes an ultrasonic actuator having an ultrasonic element and configured to irradiate the examinee's eye with the ultrasonic wave, and current adjustment means configured to adjust a current applied to the ultrasonic element to control the sound pressure or acoustic radiation pressure of the ultrasonic wave. With this configuration, the ultrasonic tonometer solving at least one of typical problems can be provided. For example, the ultrasonic tonometer capable of properly irradiating the examinee's eye with the ultrasonic wave can be provided.

4 Claims, 11 Drawing Sheets

(58) Field of Classification Search
CPC ............ A61B 5/031; A61B 2560/0219; A61B 2560/0252; A61B 2560/0418; A61B 2562/0238; A61B 3/1241; A61B 3/14; A61B 5/01; A61B 5/14532; A61B 5/14539; A61B 5/14546; A61B 5/1455; A61B 5/14555; A61B 5/1486; A61B 5/18; A61B 5/416; A61B 5/445; A61B 8/56; A61B 2560/0214; A61B 2562/12; A61B 3/0025; A61B 3/0058; A61B 3/10; A61B 3/185; A61B 5/14507; A61B 5/412; A61B 8/10; A61B 2560/0242; A61B 3/0041; A61B 5/0205; A61B 5/024; A61B 5/11; A61B 5/112; A61B 5/1123; A61B 5/14551; A61B 5/16; A61B 5/291; A61B 5/293; A61B 5/369; A61B 5/375; A61B 5/377; A61B 5/38; A61B 5/383; A61B 5/389; A61B 5/398; A61B 5/4082; A61B 5/4088; A61B 5/4806; A61B 5/4809; A61B 5/4815; A61B 5/4818; A61B 5/6802; A61B 5/6803; A61B 5/681; A61B 5/6824; A61B 5/72; A61B 8/02; A61B 8/4427; A61B 8/488; A61B 2017/00199; A61B 2017/00694; A61B 2017/00973; A61B 3/152; A61B 17/32; A61B 3/0091; A61B 3/13; A61B 5/411; A61B 5/6821; A61B 3/1005; A61B 3/12; A61B 3/1233; A61B 3/145; A61B 5/0077; A61B 5/02216; A61B 5/6885; A61B 5/7278; A61F 9/0017; A61F 9/0026; A61F 2009/0035; A61F 2009/00846; A61F 2009/00872; A61F 2009/00897; A61F 9/008; A61F 9/007; A61F 9/00781; A61F 9/013
See application file for complete search history.

(56) References Cited

U.S. PATENT DOCUMENTS

| | | |
|---|---|---|
| 2006/0001334 A1 | 1/2006 | Shiba |
| 2009/0275819 A1* | 11/2009 | Miwa ........................ A61B 8/10 |
| | | 600/399 |
| 2018/0069574 A1* | 3/2018 | Kondo ........................ H03F 3/72 |

FOREIGN PATENT DOCUMENTS

| | | |
|---|---|---|
| JP | 2006-020018 A | 1/2006 |
| JP | 2009-268651 A | 11/2009 |
| JP | 2015-008955 A | 1/2015 |

* cited by examiner

ULTRASONIC TONOMETER

TECHNICAL FIELD

The present disclosure relates to an ultrasonic tonometer for measuring the eye pressure of an examinee's eye by means of an ultrasonic wave.

BACKGROUND ART

An air-injection tonometer has been still generally known as a non-contact tonometer. The air-injection tonometer detects a cornea deformation state upon injection of air to a cornea and the pressure of air injected to the cornea, thereby converting an air pressure in a predetermined deformation state into an eye pressure.

As the non-contact tonometer, an ultrasonic tonometer for measuring an eye pressure by means of an ultrasonic wave has been proposed (see Patent Literature 1). The ultrasonic tonometer of Patent Literature 1 detects a cornea deformation state upon radiation of a cornea with the ultrasonic wave and the pressure of radiation to the cornea, thereby converting a radiation pressure in a predetermined deformation state into an eye pressure.

As the ultrasonic tonometer, a device configured to measure an eye pressure based on a relationship between the characteristics (an amplitude, a phase) of a reflected wave from a cornea and the eye pressure has been proposed (see Patent Literature 2).

CITATION LIST

Patent Literature

PATENT LITERATURE 1: JP-A-5-253190
PATENT LITERATURE 2: JP-A-2009-268651

SUMMARY OF INVENTION

However, in the typical device, the cornea of the examinee's eye cannot be properly irradiated with the ultrasonic wave. For example, in the device of Patent Literature 1, the cornea cannot be properly irradiated with the ultrasonic wave, and the ultrasonic wave at such a level that the cornea is flattened or depressed cannot be actually applied to the examinee's eye. Moreover, in, e.g., the device of Patent Literature 2, the cornea cannot be properly irradiated with the ultrasonic wave, and the characteristics of the reflected wave cannot be sufficiently detected.

There are also other problems. In an ultrasonic type (an acoustic radiation pressure type), a cornea can be deformed in a short period of time, and therefore, there is an advantage that eye pressure measurement can be performed in a short period of time and a burden on a patient can be reduced. However, when the cornea is deformed in a short period of time, a detection signal for detecting a cornea deformation state also rapidly changes. For this reason, influence of, e.g., unexpected noise caused in the detection signal is more likely to be provided, leading to a probability that eye pressure measurement accuracy is degraded.

A technical object of the present disclosure is to provide an ultrasonic tonometer solving at least one of the typical problems.

For solving the above-described problems, the present disclosure includes the following configurations.

(1) An ultrasonic tonometer for measuring an eye pressure of an examinee's eye by means of an ultrasonic wave, including: an ultrasonic actuator having an ultrasonic element and configured to irradiate the examinee's eye with the ultrasonic wave; and current adjustment means configured to adjust a current applied to the ultrasonic element to control a sound pressure or acoustic radiation pressure of the ultrasonic wave.

(2) An ultrasonic tonometer for measuring an eye pressure of an examinee's eye by means of an ultrasonic wave, including: irradiation means having an ultrasonic element and configured to irradiate the examinee's eye with the ultrasonic wave; and control means configured to control the irradiation means, in which the control means corrects an application frequency for the ultrasonic element.

(3) An ultrasonic tonometer for measuring an eye pressure of an examinee's eye by means of an ultrasonic wave, including: irradiation means having an ultrasonic element and configured to irradiate the examinee's eye with the ultrasonic wave; and control means configured to control the irradiation means, in which the control means corrects a resonant frequency of the irradiation means.

(4) An ultrasonic tonometer for measuring an eye pressure of an examinee's eye by means of an ultrasonic wave, including: irradiation means having an ultrasonic element and configured to irradiate the examinee's eye with the ultrasonic wave; and control means configured to control the irradiation means, in which the control means controls a sound pressure or acoustic radiation pressure of the ultrasonic wave output by the irradiation means to change eye pressure measurement accuracy.

DESCRIPTION OF EMBODIMENTS

First Embodiment

Figure 1:
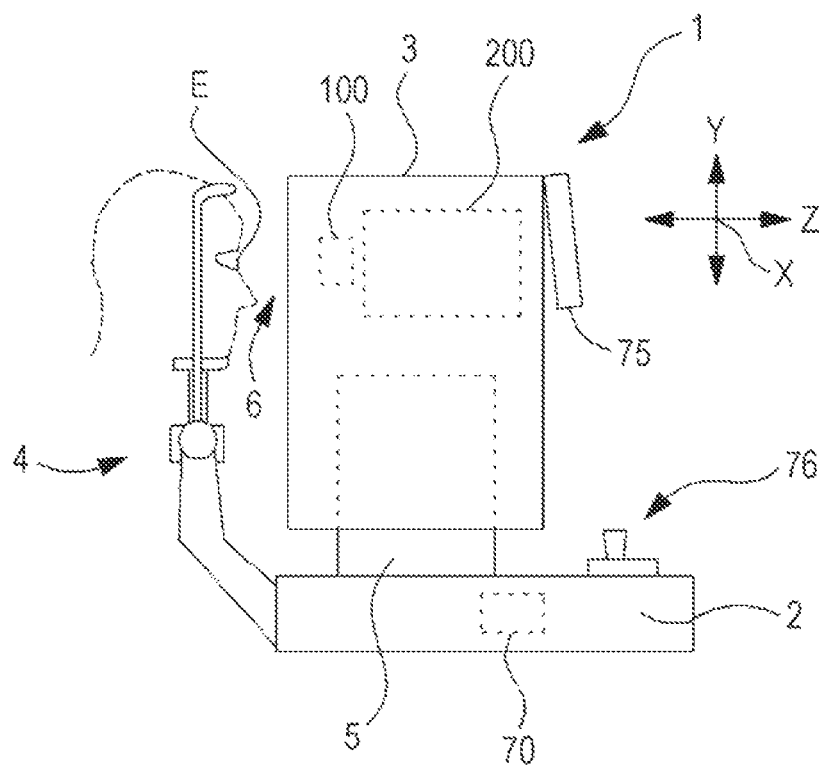
FIG. 1 is an external view of an ultrasonic tonometer.

Hereinafter, a first embodiment according to the present disclosure will be described. An ultrasonic tonometer (e.g., an ultrasonic tonometer 1) of the first embodiment measures the eye pressure of an examinee's eye by means of an ultrasonic wave. The ultrasonic tonometer includes, for example, an ultrasonic actuator (e.g., an ultrasonic actuator 100) and a current adjuster (e.g., a current adjuster 83). The ultrasonic actuator has an ultrasonic element (e.g., an ultrasonic element 110), and irradiates the examinee's eye with the ultrasonic wave. The current adjuster adjusts a current applied to the ultrasonic element. Thus, a sound pressure or an acoustic radiation pressure output from the ultrasonic actuator can be stabilized, and eye pressure measurement can be suitably performed. For example, the ultrasonic tonometer irradiates the examinee's eye with the stable sound pressure or acoustic radiation pressure so that a cornea can be suitably deformed (brought into an applanation state).

Note that the ultrasonic tonometer may include a controller (e.g., a controller 70) and an acquirer (a detector 500). The controller controls the current adjuster, for example. The acquirer acquires current information regarding the level of current flowing in the ultrasonic actuator. In this case, the controller may control the current adjuster based on the current information. For example, the controller may control the current adjuster such that a predetermined current flows in the ultrasonic actuator. With this configuration, the output of the ultrasonic actuator is stabilized.

Note that the acquirer may acquire the current information by detecting the value of current or voltage applied to the ultrasonic element or a resistance value of the ultrasonic element. In this case, a current meter, a voltage meter or the like may be used, for example. Moreover, the acquirer may acquire the current information by detecting the output of the ultrasonic actuator.

Note that the current adjuster may include a variable impedance section (e.g., a variable impedance section 84). In this case, the controller may change the impedance of the variable impedance section to adjust current. For example, the impedance of the variable impedance section connected in series with the ultrasonic actuator is changed so that the current flowing in the ultrasonic actuator can be adjusted.

Second Embodiment

Hereinafter, a second embodiment according to the present disclosure will be described. An ultrasonic tonometer (e.g., an ultrasonic tonometer 1) of the second embodiment measures the eye pressure of an examinee's eye by means of an ultrasonic wave. The ultrasonic tonometer includes, for example, an irradiator (e.g., an ultrasonic actuator 100) and a controller (e.g., a controller 70). The irradiator has an ultrasonic element (e.g., an ultrasonic element 110), and irradiates the examinee's eye with the ultrasonic wave. The controller controls irradiation to correct an application frequency for the ultrasonic element. With this configuration, a sound pressure (or an acoustic radiation pressure) output to the examinee's eye can be stabilized.

Note that the controller may correct the application frequency according to a temporal change in the resonant frequency of the irradiator. For example, the controller may correct the application frequency to approach the resonant frequency of the irradiator. A voltage with the application frequency close to the resonant frequency of the irradiator is applied so that the irradiator can resonate and a sufficient sound pressure or acoustic radiation pressure for eye pressure measurement can be output. Needless to say, the controller may adjust, if possible, the application frequency for the ultrasonic element to the resonant frequency of the irradiator.

Note that the application frequency may be the frequency of the voltage applied to the ultrasonic element. For example, in a case where the waveform of the voltage to be applied is a burst wave, the application frequency may be the frequency of the burst wave.

Note that the present device may further includes a detector (e.g., a detector 500) configured to detect the output of the irradiator. In this case, the controller corrects the application frequency based on a detection result of the detector. For example, the controller may correct the application frequency such that the output (the sound pressure or the acoustic radiation pressure) of the irradiator increases. The detector may detect the ultrasonic wave output from the irradiator, or may detect vibration of the irradiator. The controller may correct the application frequency based on the amplitude of, e.g., the ultrasonic wave or vibration detected by the detector.

Note that the controller may display the corrected application frequency on a display (e.g., a display 75). With this configuration, a change in the application frequency can be checked.

Note that the controller may correct the resonant frequency of the irradiator. For example, the ultrasonic tonometer may further include a clamper (e.g., a back mass 132, a sonotrode 131, a driver 600 or the like) configured to clamp the ultrasonic element. In this case, the controller may adjust the clamp pressure of the clamper, and in this manner, the resonant frequency may be stabilized. With this configuration, an increase in a difference between the resonant frequency and the application frequency is suppressed so that the sound pressure of the irradiator can be stabilized.

Note that the controller may display the corrected resonant frequency on the display. With this configuration, it can be easily checked whether or not the resonant frequency is stabilized.

Third Embodiment

Hereinafter, a third embodiment according to the present disclosure will be described. An ultrasonic tonometer of the third embodiment measures the eye pressure of an examinee's eye by means of an ultrasonic wave. The ultrasonic tonometer includes, for example, an irradiator (e.g., an ultrasonic actuator 100) and a controller (e.g., a controller 70). The irradiator has an ultrasonic element, and irradiates the examinee's eye with the ultrasonic wave. The controller controls the irradiator. The controller controls the sound pressure or acoustic radiation pressure of the ultrasonic wave output by the irradiator to change eye pressure measurement accuracy. With this configuration, the eye pressure can be measured with suitable measurement accuracy.

Note that the controller may control the rate (speed) of increase in the sound pressure or the acoustic radiation pressure, thereby changing the eye pressure measurement accuracy. For example, in a case where the eye pressure is measured based on elapsed time when a cornea changes to a predetermined shape by the acoustic radiation pressure, the rate of increase in the sound pressure or the acoustic radiation pressure to the time may be slowed. With this configuration, time until the cornea deforms to the predetermined shape increases, and therefore, deformation of the cornea can be detected with favorable accuracy.

Note that the controller may control a voltage, current, or frequency applied to the ultrasonic element. With this configuration, the rate of increase in the sound pressure or the acoustic radiation pressure can be easily changed.

The controller may perform switching between a first measurement mode (e.g., a screening mode) for roughly measuring the eye pressure of the examinee's eye and a second measurement mode (a high-accuracy measurement mode) for measuring the eye pressure with higher accuracy (higher precision) than that of the first measurement mode.

With this configuration, the controller can perform eye pressure measurement with different levels of accuracy. For example, the ultrasonic tonometer can perform eye pressure measurement with first measurement accuracy and second measurement accuracy.

The controller may perform switching to the second measurement mode based on the eye pressure measured in the first measurement mode. For example, in a case where the eye pressure measured in the first measurement mode is lower than a predetermined value, the controller may transition to measurement in the second measurement mode. In a case where the eye pressure is higher than the predetermined value, the controller may perform no measurement in the second measurement mode. With this configuration, an increase in measurement time and a burden on an examinee for measuring a more detailed eye pressure value can be prevented.

The controller may change the measurement accuracy in the second measurement mode based on the eye pressure measured in the first measurement mode.

For example, the controller may increase the measurement accuracy in the second measurement mode as the eye pressure value measured in the first measurement mode decreases. With this configuration, the eye pressure can be measured with accuracy suitable for each examinee.

First Example

Hereinafter, a first example according to the present disclosure will be described. An ultrasonic tonometer of the first example measures, for example, the eye pressure of an examinee's eye in a non-contact manner by using an ultrasonic wave. For example, the ultrasonic tonometer measures the eye pressure by optically or acoustically detecting, e.g., a change in the shape of the examinee's eye or vibration upon irradiation of the examinee's eye with the ultrasonic wave. For example, the ultrasonic tonometer calculates the eye pressure based on, e.g., ultrasonic wave output information when a cornea is continuously irradiated with a pulse wave or a burst wave and deforms to a predetermined shape. The output information is, for example, the sound pressure, acoustic radiation pressure, irradiation time (e.g., elapsed time after a trigger signal has been input), or frequency of the ultrasonic wave. Note that in the case of deforming the cornea of the examinee's eye, the sound pressure, acoustic radiation pressure, or acoustic flow of the ultrasonic wave is used, for example.

FIG. 1 illustrates a device appearance. An ultrasonic tonometer 1 includes, for example, abase 2, a housing 3, a face supporter 4, and a driver 5. In the housing 3, e.g., an ultrasonic actuator 100 and an optical unit 200 as described later are arranged. The face supporter 4 supports a face with examinee's eyes. The face supporter 4 is, for example, placed on the base 2. The driver 5 moves the housing 3 relative to the base 2 for alignment, for example.

Figure 2:
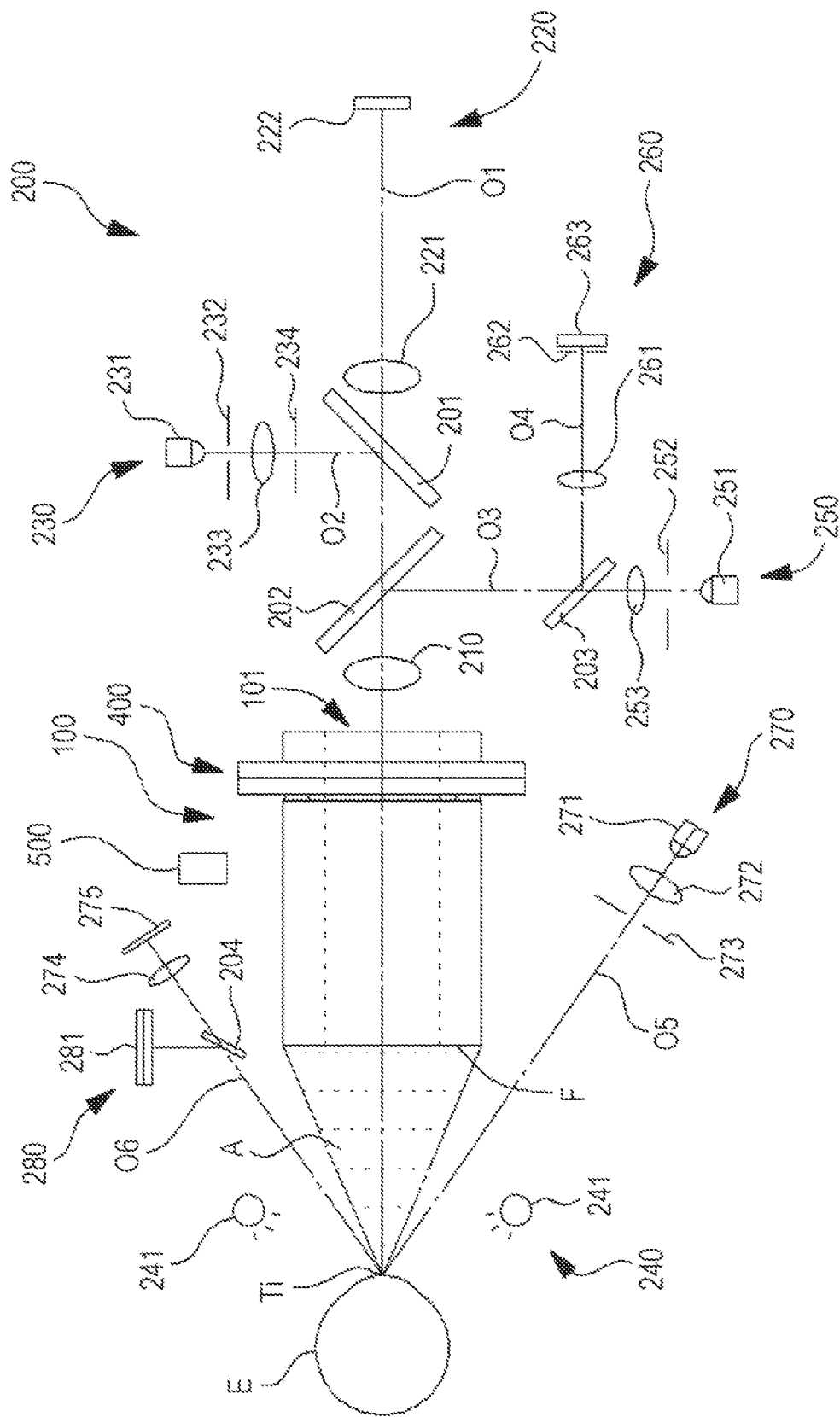
FIG. 2 is a schematic view of the inside of a housing.

FIG. 2 is a schematic view of a main configuration in the housing. In the housing 3, e.g., the ultrasonic actuator 100 and the optical unit 200 are arranged. The ultrasonic actuator 100 and the optical unit 200 will be sequentially described with reference to FIG. 2.

The ultrasonic actuator 100 irradiates an examinee's eye E with an ultrasonic wave, for example. For example, the ultrasonic actuator 100 irradiates a cornea with the ultrasonic wave, thereby generating an acoustic radiation pressure on the cornea. The acoustic radiation pressure is, for example, force acting in a sound wave travel direction. The ultrasonic tonometer 1 of the present example deforms the cornea by utilizing this acoustic radiation pressure, for example. Note that an ultrasonic unit of the present example is in a cylindrical shape, and in a center opening 101, the optical axis O1 of the optical unit 200 described later is arranged.

Figure 3A:
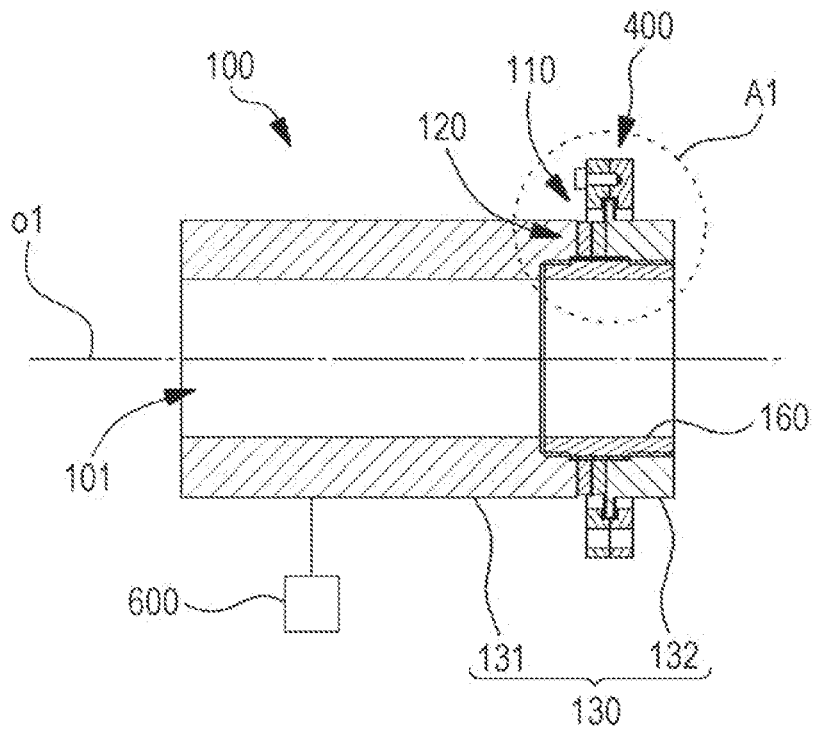
FIG. 3A is a schematic view of the configuration of an ultrasonic actuator.
Figure 3B:
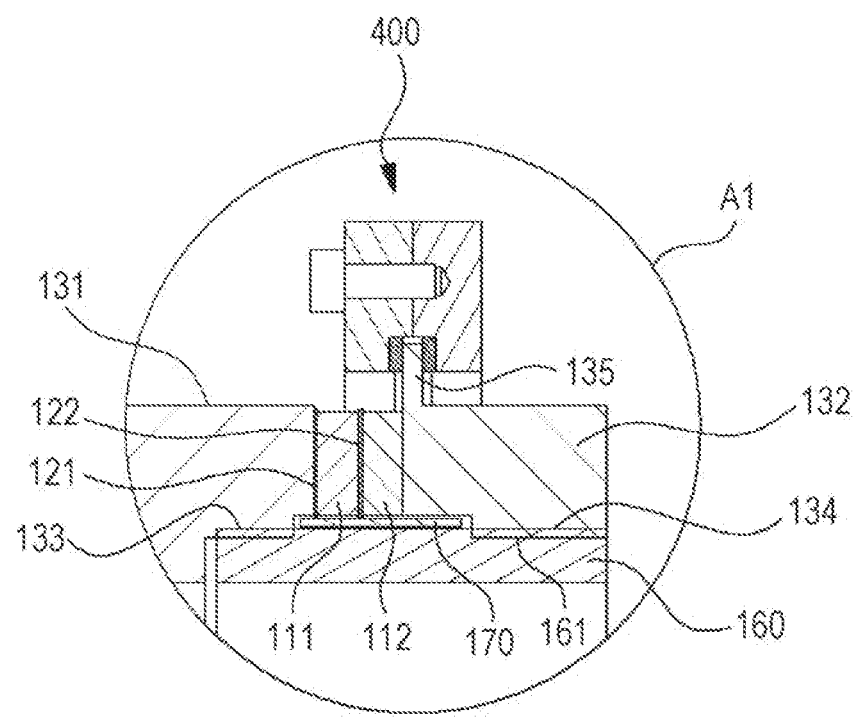
FIG. 3B is a schematic view of the configuration of the ultrasonic actuator.

FIG. 3A is a sectional view of a schematic configuration of the ultrasonic actuator 100. FIG. 3B illustrates, in closeup, the state of an area A1 illustrated in FIG. 3A. The ultrasonic actuator 100 of the present example is a so-called Langevin transducer. The ultrasonic actuator 100 includes, for example, an ultrasonic element 110, an electrode 120, amass member 130, and a fastening member 160. The ultrasonic element 110 generates the ultrasonic wave. The ultrasonic element 110 may be a voltage element (e.g., piezoelectric ceramics) or a magnetostriction element. The ultrasonic element 110 of the present example is in a ring shape. For example, the ultrasonic element 110 may be configured such that multiple piezoelectric elements are stacked on each other. In the present example, a stack of two piezoelectric elements (e.g., a piezoelectric element 111 and a piezoelectric element 112) is used as the ultrasonic element 110. For example, the electrode 120 (an electrode 121 and an electrode 122) is connected to each of these two piezoelectric elements. The electrode 121 and the electrode 122 of the present example are in a ring shape, for example.

The mass member 130 sandwiches the ultrasonic element 110, for example. The mass member 130 sandwiches the ultrasonic element 110 to increase the tensile strength of the ultrasonic element 110 such that high resistance to vibration is obtained, for example. Accordingly, high ultrasonic wave output can be generated. For example, the mass member 130 may be a metal block. For example, the mass member 130 includes a sonotrode (also called a horn or a front mass) 131 and a back mass 132.

The sonotrode 131 is a mass member arranged in the front (an examinee's eye side) of the ultrasonic element 110. The sonotrode 131 causes the ultrasonic wave generated by the ultrasonic element 110 to propagate in air. The sonotrode 131 of the present example is in a cylindrical shape. An internal thread portion 133 is formed at part of an inner circular portion of the sonotrode 131. The internal thread portion 133 engages with an external thread portion 161 formed at the later-described fastening member 160. Note that the sonotrode 131 may have a shape for converging the ultrasonic wave. For example, an examinee's-eye-side end surface of the sonotrode 131 may be inclined to an opening 101 side to have a tapered shape. The sonotrode 131 may be a cylinder having a non-uniform thickness. For example, the sonotrode 131 may have a shape of which outer and inner diameters change in a cylinder longitudinal direction.

The back mass 132 is a mass member arranged in the back of the ultrasonic element 110. The back mass 132 and the sonotrode 131 together sandwich the ultrasonic element 110. The back mass 132 is in a cylindrical shape, for example. An internal thread portion 134 is formed at part of an inner circular portion of the back mass 132. The internal thread portion 134 engages with the external thread portion 161 of the later-described fastening member 160. Moreover, the back mass 132 includes a flange portion 135. The flange portion 135 is held by an attachment portion 400.

The fastening member 160 fastens the mass member 130 and the ultrasonic element 110 sandwiched by the mass member 130, for example. For example, the fastening member 160 is a hollow bolt. For example, the fastening member 160 is in a cylindrical shape, and at an outer circular portion thereof, includes the external thread portion 161. The external thread portion 161 of the fastening member 160 engages with the internal thread portions 133, 134 formed inside the sonotrode 131 and the back mass 132. The sonotrode 131 and the back mass 132 are, by the fastening member 160, fastened in the direction of pulling against each other. Accordingly, the ultrasonic element 110 sandwiched between the sonotrode 131 and the back mass 132 is fastened, and pressure is on the ultrasonic element 110.

Note that the ultrasonic actuator 100 may include an insulating member 170. The insulating member 170 prevents, for example, contact of the electrode 120 or the ultrasonic element 110 with the fastening member 160. The insulating member 170 is arranged between the electrode 120 and the fastening member 160, for example. For example, the insulating member 170 is in a sleeve shape.

<Optical Unit>

The optical unit 200 performs examinee's eye observation or measurement (see FIG. 2), for example. The optical unit 200 includes, for example, an objective system 210, an observation system 220, a fixation target projection system 230, a target projection system 250, a deformation detection system 260, a dichroic mirror 201, a beam splitter 202, a beam splitter 203, and a beam splitter 204.

The objective system 210 is, for example, an optical system for taking light into the optical unit 200 from the outside of the housing 3 or for irradiating the outside of the housing 3 with light from the optical unit 200. The objective system 210 includes an optical element, for example. The objective system 210 may include an optical element (e.g., an objective lens or a relay lens).

An illuminating optical system 240 illuminates the examinee's eye. For example, the illuminating optical system 240 illuminates the examinee's eye with infrared light. The illuminating optical system 240 includes an illuminating light source 241, for example. The illuminating light source 241 is, for example, arranged diagonally in the front of the examinee's eye. The illuminating light source 241 emits the infrared light, for example. The illuminating optical system 240 may include multiple illuminating light sources 241.

The observation system 220 captures an observation image of the examinee's eye, for example. The observation system 220 captures an image of an anterior segment of the examinee's eye, for example. The observation system 220 includes, for example, a light receiving lens 221 and a light receiving element 222. For example, the observation system 220 receives light from the illuminating light source 241 after the light has been reflected on the examinee's eye. The observation system receives a reflected light flux about the optical axis O1 from the examinee's eye, for example. For example, the reflected light from the examinee's eye passes the opening 101 of the ultrasonic actuator 100, and is received by the light receiving element 222 through the objective system 210 and the light receiving lens 221.

The fixation target projection system 230 projects a fixation target on the examinee's eye, for example. The fixation target projection system 230 includes, for example, a target light source 231, a diaphragm 232, a light projecting lens 233, and a diaphragm 234. Light from the target light source 231 passes, along an optical axis O2, the diaphragm 232, the light projecting lens 233, the diaphragm 232 and the like, and is reflected by the dichroic mirror 201. The dichroic mirror 201 causes, for example, the optical axis O2 of the fixation target projection system 230 to be coaxial with the optical axis O1. After having been reflected by the dichroic mirror 201, the light from the target light source 231 passes the objective system 210 along the optical axis O1, and the examinee's eye is irradiated with such light. An examinee fixates the target provided by the fixation target projection system 230, and therefore, an examinee's visual line is stabilized.

The target projection system 250 projects a target on the examinee's eye, for example. The target projection system 250 projects a target for XY-alignment on the examinee's eye. The target projection system 250 includes, for example, a target light source (e.g., may be an infrared light source) 251, a diaphragm 252, and a light projecting lens 253. Light from the target light source 251 passes, along an optical axis O3, the diaphragm 252 and the light projecting lens 253, and is reflected by the beam splitter 202. The beam splitter 202 causes, for example, the optical axis O3 of the target projection system 250 to be coaxial with the optical axis O1. After having been reflected by the beam splitter 202, the light from the target light source 251 passes the objective system 210 along the optical axis O1, and the examinee's eye is irradiated with such light. After the examinee's eye has been irradiated with the light from the target light source 251, such light is reflected on the examinee's eye, and passes the objective system 210, the light receiving lens 221 and the like again along the optical axis O1. Then, the light is received by the light receiving element 222. The target of which light has been received by the light receiving element is, for example, utilized for XY-alignment. In this case, the target projection system 250 and the observation system 220 function as XY-alignment detection means, for example.

The deformation detection system 260 detects the corneal shape of the examinee's eye, for example. For example, the deformation detection system 260 detects deformation of the cornea of the examinee's eye. The deformation detection system 260 includes, for example, a light receiving lens 261, a diaphragm 262, and a light receiving element 263. For example, the deformation detection system 260 may detect deformation of the cornea based on cornea reflected light received by the light receiving element 263. For example, the deformation detection system 260 may detect deformation of the cornea by receiving, by the light receiving element 263, the light emitted from the target light source 251 and reflected on the cornea of the examinee's eye. For example, the cornea reflected light passes the objective system 210 along the optical axis O1, and is reflected by the beam splitter 202 and the beam splitter 203. Then, the cornea reflected light passes the light receiving lens 261 and the diaphragm 262 along an optical axis O4, and is received by the light receiving element 263.

The deformation detection system 260 may detect a cornea deformation state based on the level of a light receiving signal of the light receiving element 236, for example. For example, the deformation detection system 260 may detect that the cornea is brought into an applanation state when the amount of light received by the light receiving element 236 reaches the maximum amount. In this case, the deformation detection system 260 is set such that the light receiving amount is maximized when the cornea of the examinee's eye is brought into the applanation state, for example.

Note that the deformation detection system 260 may be an anterior segment cross-sectional image capturing unit such as an OCT or a shine proof camera. For example, the deformation detection system 260 may detect the amount or speed of deformation of the cornea.

A corneal thickness measurement system 270 measures the corneal thickness of the examinee's eye, for example. The corneal thickness measurement system 270 may include, for example, a light source 271, a light projecting lens 272, a diaphragm 273, a light receiving lens 274, and a light receiving element 275. For example, light from the light source 271 passes the light projecting lens 272 and the diaphragm 273 along an optical axis O5, and the examinee's eye is irradiated with such light. Then, the light reflected on the examinee's eye is condensed by the light receiving lens 274 along an optical axis O6, and is received by the light receiving element 275.

A Z-alignment detection system 280 detects an alignment state in a Z-direction, for example. The Z-alignment detection system 280 includes a light receiving element 281, for example. The Z-alignment detection system 280 may detect the alignment state in the Z-direction by detecting the reflected light from the cornea, for example. For example, the Z-alignment detection system may receive the reflected light generated by reflection of the light from the light source 271 on the cornea of the examinee's eye. In this case, the Z-alignment detection system 280 may receive a raster generated by reflection of the light from the light source 271 on the cornea of the examinee's eye. As described above, the light source 271 may also serve as a light source for Z-alignment detection. For example, the light emitted from the light source 271 and reflected on the cornea is reflected by the beam splitter 204 along the optical axis O6, and is received by the light receiving element 281.

<Detector>

A detector 500 detects the output of the ultrasonic actuator 100, for example. The detector 500 is a sensor such as an ultrasonic sensor, a displacement sensor, or a pressure sensor. The ultrasonic sensor detects the ultrasonic wave generated from the ultrasonic actuator 100. The displacement sensor detects displacement of the ultrasonic actuator 100. The displacement sensor may continuously detect displacement to detect vibration when the ultrasonic actuator 100 generates the ultrasonic wave.

As illustrated in FIG. 2, the detector 500 is arranged outside an ultrasonic wave irradiation path A. The irradiation path A is, for example, a region connecting a front surface F of the ultrasonic actuator 100 and an ultrasonic wave irradiation target Ti. The detector 500 is, for example, arranged in the side or back of the ultrasonic actuator 100. In a case where the detector 500 is arranged in the side of the ultrasonic actuator 100 as in the present example, observation of the examinee's eye by the observation system 220 is easily performed. In a case where the ultrasonic sensor is used as the detector 500, the detector 500 detects the ultrasonic wave leaking from the side or back of the ultrasonic actuator 100. In a case where the displacement sensor is used as the detector 500, the detector 500 detects displacement of the ultrasonic actuator 100 from the side or back of the ultrasonic actuator 100. For example, the displacement sensor irradiates the ultrasonic actuator 100 with laser light, and based on reflected laser light, detects displacement of the ultrasonic actuator 100. A signal detected by the detector 500 is transmitted to a controller.

<Controller>

Next, the configuration of a control system will be described with reference to FIG. 5. A controller 70 performs entire device control and arithmetic processing for a measurement value, for example. The controller 70 is, for example, implemented by a general central processing unit (CPU) 71, a general ROM 72, and a general RAM 73. The ROM 72 stores various programs, initial values and the like for controlling operation of the ultrasonic tonometer 1. The RAM 73 temporarily stores various types of information. Note that the controller 70 may include a single controller or multiple controllers (or multiple processors). The controller 70 may be, for example, connected to the driver 5, a storage 74, a display 75, an operator 76, the ultrasonic actuator 100, the optical unit 200, and the detector 500.

The storage 74 is a non-transitory storage medium capable of holding stored contents even when a power supply is cut off. For example, a hard disk drive, a flash ROM, or a detachable USB memory can be used as the storage 74.

The display 75 displays an examinee's eye measurement result, for example. The display 75 may have a touch panel function.

The operator 76 receives various operation instructions from an examiner. The operator 76 outputs, to the controller 70, an operation signal corresponding to the input operation instruction. For example, at least any of user interfaces such as a touch panel, a mouse, a joy stick, and a keyboard may be used as the operator 76. Note that in a case where the display 75 is a touch panel, the display 75 may function as the operator 76.

<Electric Circuit>

Figure 5:
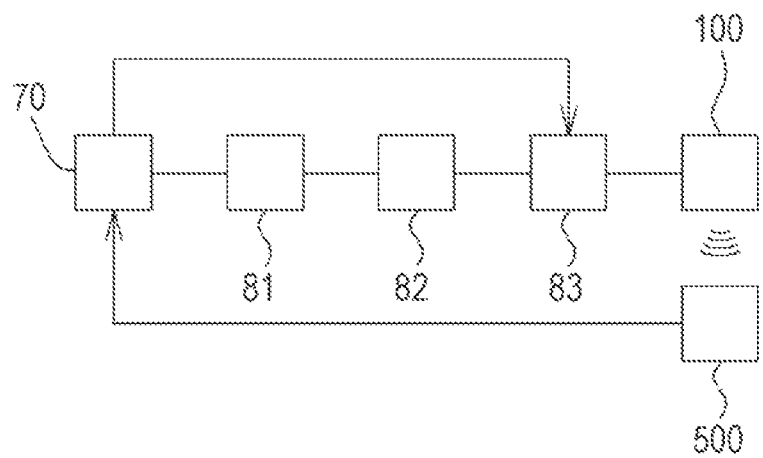
FIG. 5 is a block diagram of the configuration of an electric circuit.

FIG. 5 is a schematic diagram of an electric circuit of the present example. The ultrasonic tonometer 1 includes, for example, a signal generator 81, a signal amplifier 82, and a current adjuster 83. The signal generator 81 generates a voltage signal applied to the ultrasonic actuator 100, for example. In the present example, a voltage signal with a burst wave is generated by the signal generator 81. The voltage signal generated by the signal generator 81 is transmitted to the signal amplifier 82. The signal amplifier 82 amplifies the voltage signal generated by the signal generator 81. The signal amplifier 82 is, for example, a power amplifier. The current adjuster 83 adjusts a current flowing in the ultrasonic actuator 100, for example.

Figure 4:
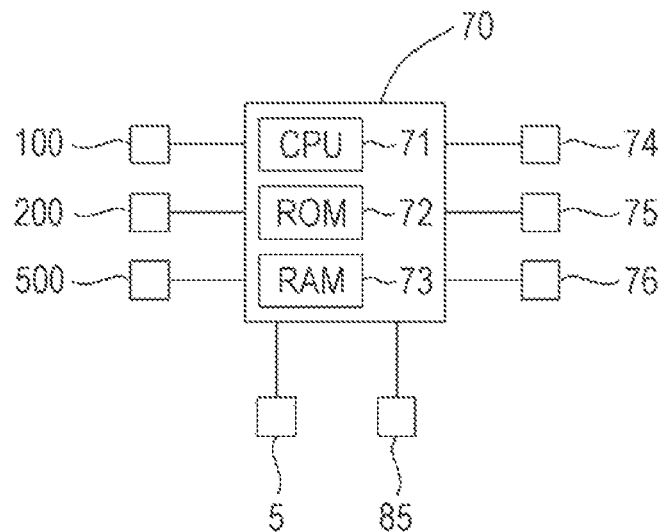
FIG. 4 is a block diagram of a control system.
Figure 6:
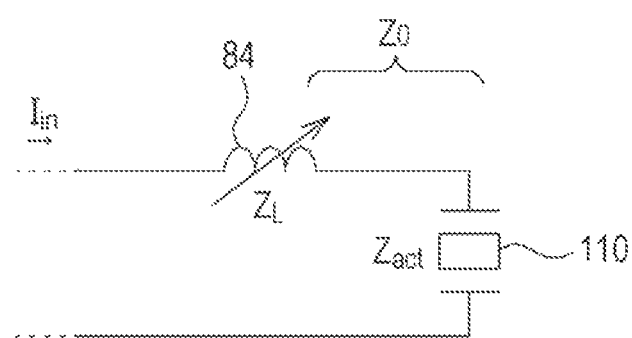
FIG. 6 is a diagram of one example of a current adjuster.

FIG. 6 is a diagram of the current adjuster 83. The current adjuster 83 has a variable impedance section 84, for example. The variable impedance section 84 is an element capable of changing an impedance. The variable impedance section 84 may be a variable inductor, for example. The variable inductor is, for example, an element capable of changing, by sliding a core (e.g., a magnet) to shift the positions of the core and a coil from each other, a magnetic permeability to change the impedance (e.g., an inductance). For example, the controller 70 moves the core by drive of a driver 85 (see FIG. 4) so that the impedance can be changed. The current adjuster 83 of the present example changes the impedance of the variable impedance section 84 to adjust the current flowing in the ultrasonic actuator 100.

The current $I_{in}$ flowing in the ultrasonic actuator 100 changes according to the impedance $Z_0$ of the entire circuit. For example, as the impedance $Z_0$ of the entire circuit decreases, the current is more likely to flow in the circuit, and therefore, the current $I_{in}$ flowing in the ultrasonic actuator 100 increases. Conversely, as the impedance $Z_0$ of the entire circuit increases, the current is less likely to flow in the circuit, and therefore, the current $I_{in}$ flowing in the ultrasonic actuator 100 decreases. In the case of present example, the variable impedance section 84 and the ultrasonic actuator 100 are connected in series. Thus, the impedance $Z_0$ of the entire circuit is represented by Formula 1, assuming that the impedance of the variable impedance section 84 is $Z_L$ and the impedance of the ultrasonic actuator 100 is $Z_{act}$. Thus, the current adjuster 83 changes the impedance $Z_L$ of the variable impedance section 84 to change the impedance $Z_0$ of the entire circuit, thereby adjusting the current $I_{in}$.

$$Z_0 = Z_L + Z_{act} \quad [\text{Formula 1}]$$

For example, for increasing the current $I_{in}$ flowing in the ultrasonic actuator 100, the impedance $Z_L$ of the variable impedance section 84 is decreased. Accordingly, the impedance $Z_0$ of the entire circuit decreases, and the current $I_{in}$ increases. For decreasing the current $I_{in}$ flowing in the ultrasonic actuator 100, the impedance $Z_L$ of the variable impedance section 84 is increased. Accordingly, the impedance $Z_0$ of the entire circuit increases, and the current $I_{in}$ decreases.

Note that in the present example, a current value is adjusted based on the sound pressure output from the ultrasonic actuator 100. For example, the sound pressure P of the ultrasonic wave output from the ultrasonic actuator 100 is detected and is compared with a target sound pressure $P_0$. In a case where the sound pressure P is lower than the target sound pressure $P_0$, it is assumed that the current $I_{in}$ flowing in the ultrasonic element 110 has decreased. Thus, the controller 70 decreases the impedance $Z_L$ of the variable impedance section 84 to decrease the impedance $Z_0$ of the entire circuit and increase the current L flowing in the ultrasonic actuator 100. Conversely, in a case where the sound pressure P of the ultrasonic wave is higher than the target sound pressure $P_0$, it is assumed that the current $I_{in}$ flowing in the ultrasonic element 110 has increased. Thus, the controller 70 increases the impedance $Z_L$ of the variable impedance section 84 to increase the impedance $Z_0$ of the entire circuit and decrease the current $I_{in}$ flowing in the ultrasonic actuator 100.

For example, it is assumed that the impedance of the variable impedance section 84 at time $t_1$ before current adjustment is $Z_L(t_1)$ and the impedance of the variable impedance section 84 at time $t_2$ after current adjustment is $Z_L(t_2)$. In this case, the impedance $Z_L(t_2)$ can be represented by Formula 2 by means of the impedance $Z_L(t_1)$.

$$Z_L(t_2) = Z_L(t_1) \times C(t_1) \quad [\text{Formula 2}]$$

The coefficient $C(t_1)$ as described herein can be represented by Formula 3 by means of the ratio of an actual sound pressure $P(t_1)$ at the time $t_1$ to the sound pressure $P_0$ and a weighting coefficient w. Note that an experimentally-obtained numerical value is used as the coefficient w, for example.

$$C(t_1) = \frac{1}{(P(t_1)/P_0)} \times w \quad [\text{Formula 3}]$$

The current adjuster 83 sequentially changes the impedance $Z_L$ of the variable impedance section 84 based on Formula 2 and Formula 3 so that the sound pressure P of the ultrasonic wave output from the ultrasonic actuator 100 can approach the target sound pressure $P_0$. Thus, the ultrasonic actuator 100 can irradiate the examinee's eye with the ultrasonic wave with a stable sound pressure.

<Adjustment of Current Value>

Figure 7:
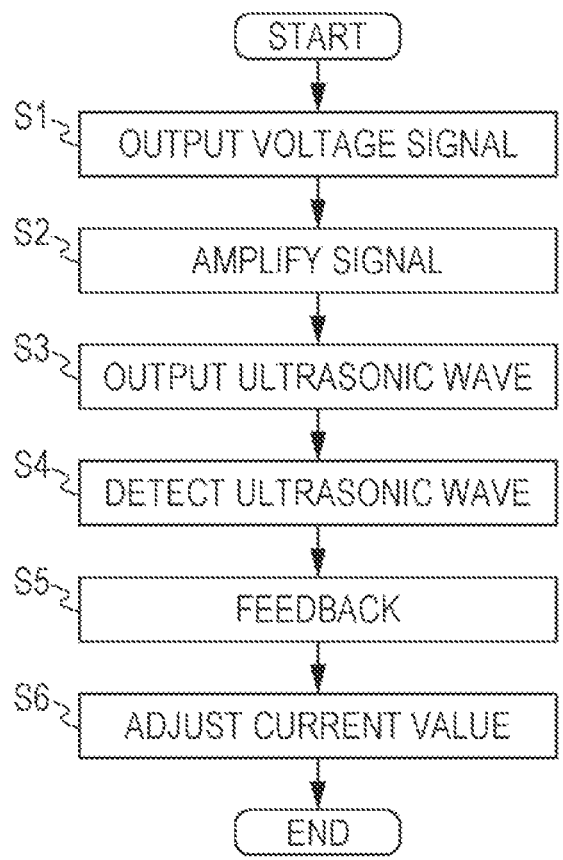
FIG. 7 is a flowchart of control operation.

Hereinafter, current value adjustment control in the present example will be described based on FIG. 7.

(Step S1: Voltage Signal Output)

First, the controller 70 controls the signal generator 81 to output a waveform signal. The signal generator 81 outputs the voltage signal with the burst wave based on a command signal from the controller 70.

(Step S2: Signal Amplification)

The voltage signal output from the signal generator 81 is input to the signal amplifier 82. The signal amplifier 82 amplifies the input voltage signal.

(Step S3: Ultrasonic Wave Output)

The voltage signal amplified by the signal amplifier 82 passes the current adjuster 83, and is input to the ultrasonic actuator 100. When the voltage signal with the burst wave is applied to the ultrasonic element 110, the ultrasonic element 110 outputs the ultrasonic wave. The ultrasonic wave generated by the ultrasonic element 110 propagates in the sonotrode 131, and the examinee's eye is irradiated with such an ultrasonic wave.

(Step S4: Ultrasonic Wave Detection)

The detector 500 detects the output of the ultrasonic actuator 100. For example, the detector 500 detects the sound pressure of the ultrasonic wave irradiated from the ultrasonic actuator 100. Needless to say, the detector 500 is not limited to detection of the sound pressure, and may detect the ultrasonic wave output from, e.g., vibration of the ultrasonic actuator 100.

(Step S5: Feedback)

The detector 500 feeds back the detected ultrasonic wave output information to the controller 70. For example, the controller 70 calculates the impedance $Z_L$ after change by means of the sound pressure fed back from the detector 500 and Calculation Formulae 2 and 3.

(Step S6: Current Value Adjustment)

The controller 70 adjusts the current value. For example, the controller 70 controls the driver 85 to adjust the impedance $Z_L$ of the variable impedance section 84 to the calculated impedance. Accordingly, a current flowing on a variable impedance section 84 side in the circuit changes. As a result, the current flowing in the ultrasonic actuator 100 changes. For example, the controller 70 repeats the steps S1 to S6 to perform such adjustment that the current flowing in the ultrasonic actuator 100 becomes constant.

<Measurement Operation>

Control operation of the device having the above-described configuration will be described. First, the controller 70 aligns the ultrasonic tonometer 1 with the eye of the examinee whose face is supported on the face supporter 4. For example, the controller 70 detects a raster generated by the target projection system 250 from an anterior segment front image acquired by the light receiving element 222. The controller 70 drives the driver 5 such that the position of the raster reaches a predetermined position. Needless to say, while viewing the display 75, the examiner may manually perform alignment with the examinee's eye by means of, e.g., the operator 76. After having driven the driver 5, the controller 70 determines alignment appropriateness based on whether or not the position of the raster of the anterior segment image is at the predetermined position.

After completion of alignment with the examinee's eye E, the controller 70 measures the corneal thickness by the corneal thickness measurement system 270. For example, the controller 70 calculates the corneal thickness based on the light receiving signal received by the light receiving element 275. For example, the controller 70 may obtain, based on the light receiving signal, the corneal thickness from a position relationship between a peak value obtained by light reflected on a corneal anterior surface and a peak value obtained by light reflected on a corneal posterior surface. The controller 70 causes, e.g., the storage 74 to store the obtained corneal thickness, for example.

Subsequently, the controller 70 measures the eye pressure of the examinee's eye by using the ultrasonic actuator 100. For example, the controller 70 applies a voltage to the ultrasonic element 110, thereby irradiating the examinee's eye E with the ultrasonic wave. The controller 70 deforms the cornea by generation of the acoustic radiation pressure by the ultrasonic wave, for example. Then, the controller 70 detects the cornea deformation state by the deformation detection system 260. For example, the controller 70 detects, based on the light receiving signal of the light receiving element 263, that the cornea has deformed to the predetermined shape (the applanation or flat state). Note that the ultrasonic tonometer 1 adjusts the current by the current adjuster 83 so that the cornea can be suitably deformed to the predetermined shape by stable ultrasonic wave output.

The controller 70 calculates, for example, the eye pressure of the examinee's eye based on the acoustic radiation pressure when the cornea of the examinee's eye deforms to the predetermined shape. The acoustic radiation pressure applied to the examinee's eye is associated with the ultrasonic wave irradiation time, and increases as the ultrasonic wave irradiation time increases. Thus, the controller 70 obtains, based on the ultrasonic wave irradiation time, the acoustic radiation pressure when the cornea deforms to the predetermined shape. A relationship between the acoustic radiation pressure when the cornea deforms to the predetermined shape and the eye pressure of the examinee's eye is obtained in advance by, e.g., experiment, and is stored in, e.g., the storage 74. The controller 70 determines the eye pressure of the examinee's eye based on the acoustic radiation pressure when the cornea deforms to the predetermined shape and the relationship stored in the storage 74. Note that as in the first example, the current is adjusted by the current adjuster 83 so that the ultrasonic wave output can be stabilized. Thus, a proper correlation between the ultrasonic wave irradiation time and the acoustic radiation pressure is easily obtained.

As described above, the ultrasonic tonometer 1 of the present example adjusts the value of current applied to the ultrasonic element 110 so that the ultrasonic wave output can be stabilized and the eye pressure can be properly measured.

For example, the ultrasonic actuator 100 entirely resonates so that a high sound pressure or acoustic radiation pressure can be output. However, a resonant frequency fluctuates overtime. For this reason, if a resonant state is not proper, the sound pressure (or the acoustic radiation pressure) might gradually decrease. Thus, the current applied to the ultrasonic actuator 100 is adjusted according to a decrease in the sound pressure (or the acoustic radiation pressure), and in this manner, a stable sound pressure or acoustic radiation pressure is obtained.

Note that in the above-described example, the detector 500 detects the sound pressure of the ultrasonic wave to feed back the sound pressure to the controller 70, but is not limited to such a configuration. For example, the detector 500 may measure, by, e.g., a sampling board, a current value, a voltage value, or a resistance value in the ultrasonic actuator 100. In this case, e.g., current, voltage, or resistance value information detected by the detector 500 is fed back to the controller 70. The controller 70 controls the current adjuster 83 based on the information fed back from the detector 500, thereby adjusting the current. As described above, the detector 500 may detect not only the sound pressure or acoustic radiation pressure of the ultrasonic wave but also the information regarding the current flowing in the ultrasonic actuator 100, thereby feeding the sound pressure or the acoustic radiation pressure and the information to the controller 70. Moreover, the controller 70 may control the current adjuster 83 such that the current flowing in the ultrasonic actuator 100 reaches a predetermined value.

Note that the current adjuster 83 may include a constant current circuit. The constant current circuit is a circuit configured to constantly apply a current even when a resistance changes. For example, a constant current circuit using a transistor has been known. Using the constant current circuit, the current value can be adjusted by the electric circuit configuration without the need for special control by the controller 70. As described above, even in the case of using the constant current circuit, the current applied to the ultrasonic actuator 100 can be stabilized, and the sound pressure or acoustic radiation pressure of the ultrasonic wave applied to the examinee's eye can be stabilized.

Second Example

A second example will be described. An ultrasonic tonometer of the second example performs control operation regarding correction of an application frequency as described below. A mechanical configuration is similar to that of the first example, and therefore, the same reference numerals are used and description thereof will be omitted.

<Correction of Application Frequency>

Figure 8:
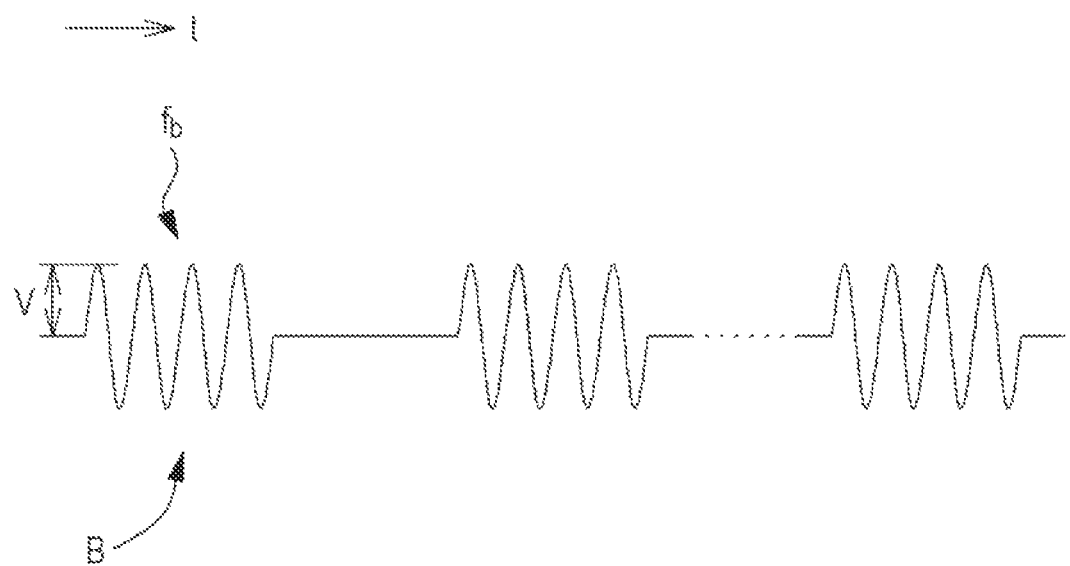
FIG. 8 is a graph of a voltage signal with a burst wave.

When an ultrasonic wave is generated by an ultrasonic actuator 100, a controller 70 applies a voltage to an ultrasonic element 110. For example, the controller 70 applies a voltage burst wave to the ultrasonic element 110. In the present example, for measuring an examinee's eye of equal to or greater than 5 mmHg, a sound pressure (or an acoustic radiation pressure) of equal to or higher than 140 dB is generated. The sound pressure (or the acoustic radiation pressure) gradually increases by continuous application of a voltage burst wave B as illustrated in FIG. 8. For example, for obtaining a high sound pressure (or a high acoustic radiation pressure), the burst wave B is continuously applied to the ultrasonic element 110 for a time of equal to or longer than 1 to 100 msec.

Figure 9:
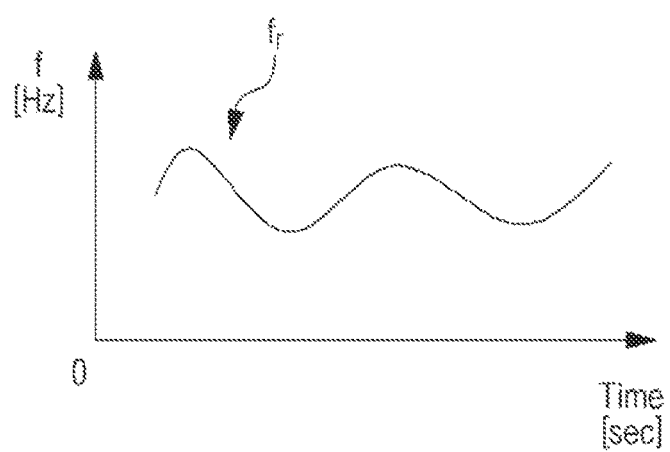
FIG. 9 is a graph of a temporal change in a resonant frequency.
Figure 10:
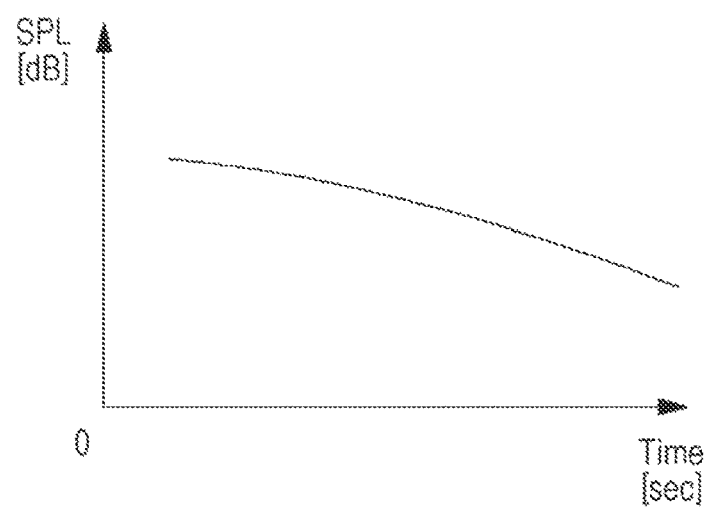
FIG. 10 is a graph of a temporal change in a sound pressure level of an ultrasonic wave.

When the ultrasonic actuator 100 of the second example resonates with a resonant frequency $f_r$, a high sound pressure or acoustic radiation pressure is output. Thus, the controller 70 applies, to the ultrasonic element 110, a burst wave with the same frequency as the resonant frequency $f_r$ of the ultrasonic actuator 100, thereby resonating the ultrasonic actuator 100. However, even in a case where a burst wave with a constant application frequency $f_b$ is applied, the resonant frequency $f_r$ of the ultrasonic actuator 100 might fluctuate over time as illustrated in FIG. 9. In this case, the resonant frequency $f_r$ and the application frequency $f_b$ shift from each other, and a proper resonant state is not obtained. As illustrated in FIG. 10, this leads to a gradual decrease in the sound pressure (or the acoustic radiation pressure). For this reason, the controller 70 of the second example corrects the application frequency $f_b$ in association with a change in the resonant frequency $f_r$, and in this manner, a stable sound pressure or acoustic radiation pressure is obtained.

Figure 11:
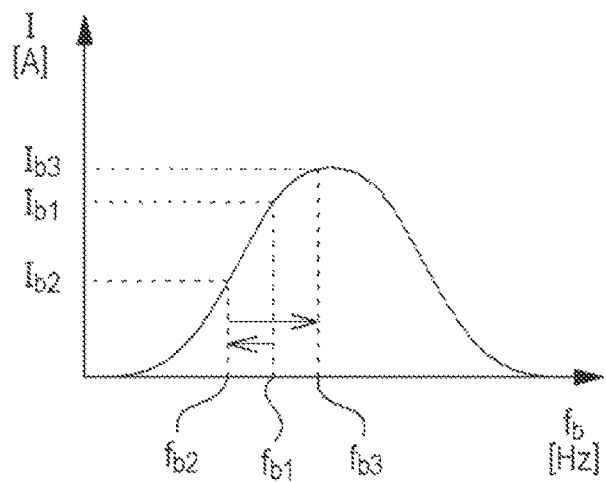
FIG. 11 is a graph of a relationship between a burst frequency and a current.

FIG. 11 is a graph of a relationship between the application frequency $f_b$ and a current flowing in the ultrasonic element 110. For example, when a predetermined level (an amplitude V) of burst wave B is applied, the controller 70 repeatedly corrects the application frequency $f_b$ such that the value of current flowing in the ultrasonic element 110 increases. In a case where the resonant state of the ultrasonic actuator 100 is proper, a resistance value of the ultrasonic element 110 decreases, and the current flowing in the ultrasonic element 110 increases. Thus, the controller 70 adjusts the application frequency $f_b$ such that the current value increases, and in this manner, the application frequency $f_b$ substantially approaches the resonant frequency $f_r$.

For example, the controller 70 searches such an application frequency $f_b$ that the current value increases. For example, the controller 70 corrects the application frequency in association with an increase/decrease in the current value measured upon a change in the application frequency $f_b$. For example, in FIG. 11, the controller 70 first applies a burst wave with an application frequency $f_{b1}$ to measure a current value $I_{b1}$ thereupon. Next, a burst wave with an application frequency $f_{b2}$ lower than the application frequency $f_{b1}$ is applied, and a current value $I_{b2}$ thereupon is measured. The current value $I_{b2}$ as described herein is smaller than the current value $I_{b1}$. Thus, a burst wave with an application frequency $f_{b3}$ higher than the application frequency $f_{b1}$ is applied next, and a current value $I_{b3}$ thereupon is measured. By repeating this process, the controller 70 corrects the application frequency $f_b$.

As described above, in the ultrasonic tonometer of the second example, the controller 70 corrects the application frequency applied to the ultrasonic element 110 so that a proper resonant state of the ultrasonic actuator 100 can be maintained and a sufficient level of sound pressure (or acoustic radiation pressure) can be stably applied to the examinee's eye. Thus, eye pressure measurement using the ultrasonic wave is allowed.

Note that the controller 70 may correct the application frequency $f_b$ based on a detection result from a detector 500. For example, in a case where the detector 500 detects the ultrasonic wave output from the ultrasonic actuator 100, the application frequency $f_b$ may be corrected such that, e.g., the sound pressure or amplitude of the ultrasonic wave increases. In a case where the detector 500 detects displacement (vibration) of the ultrasonic actuator 100, the application frequency $f_b$ may be corrected such that the amplitude of the ultrasonic actuator 100 increases. As described above, the application frequency $f_b$ is corrected such that the resonant state of the ultrasonic actuator 100 is properly maintained, and therefore, a sufficient level of sound pressure or acoustic radiation pressure can be applied to the examinee's eye.

Figure 12:
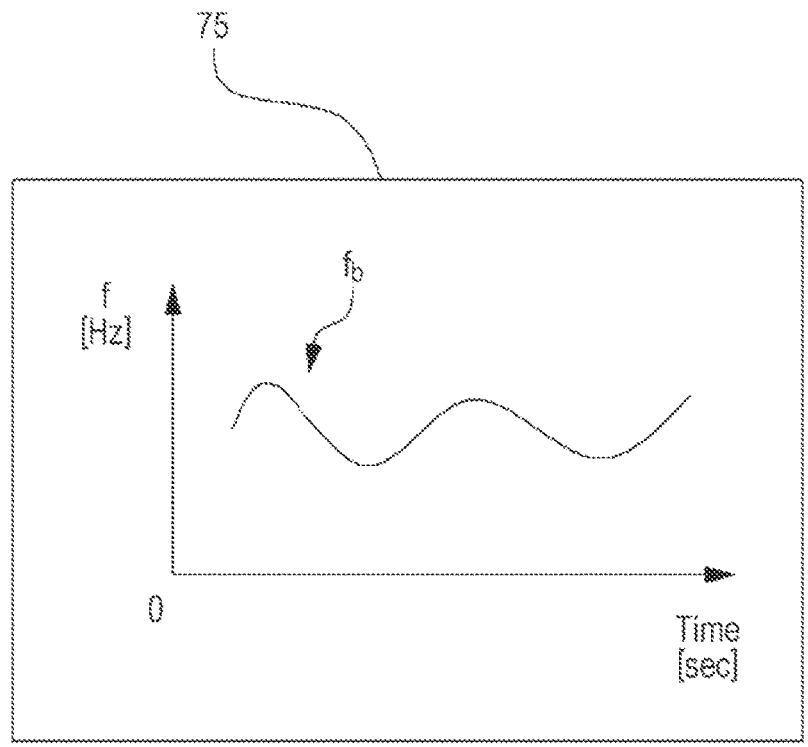
FIG. 12 is a graph of a display example of an application frequency.

Note that as illustrated in FIG. 12, the controller 70 may display the corrected application frequency $f_b$ on a display 75. Thus, the degree of correction of the frequency is easily checked. Moreover, the controller 70 may display, e.g., the amount of correction of the application frequency $f_b$ on the display 75. It may be optionally selected whether or not the application frequency $f_b$ is displayed on the display 75.

Note that it may be also optionally selected whether correction of the application frequency $f_b$ as described above is automatically performed by the controller 70 or manually performed by an examiner. For example, the controller 70 may determine, based on an operation signal output by operation of an operator 76 by the examiner, whether or not the application frequency $f_b$ is automatically corrected.

Figure 13:
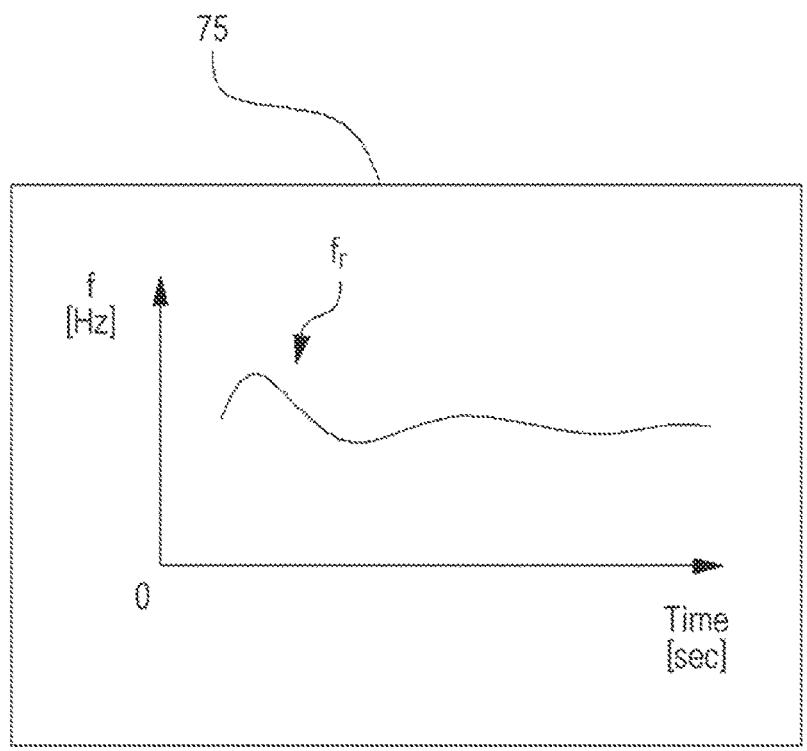
FIG. 13 is a graph of a display example of the resonant frequency.

Note that the controller 70 may correct the resonant frequency $f_r$. The controller 70 may perform correction such that the resonant frequency $f_r$ becomes constant, thereby maintaining a proper resonant state of the ultrasonic actuator 100. The method for correcting the resonant frequency includes, for example, adjustment of a clamp pressure of the ultrasonic element 110. For example, as illustrated in FIG. 3, a driver 600 configured to turn a sonotrode 131 relative to a back mass 132 is provided so that the clamp pressure of the ultrasonic element 110 can be controlled. In this case, the controller 70 controls the driver 600 to adjust the clamp pressure of the ultrasonic element 110, and therefore, fluctuation in the resonant frequency $f_r$ can be corrected. Note that in the case of correcting the resonant frequency $f_r$, the corrected resonant frequency $f_r$ may be displayed on the display 75 as illustrated in FIG. 13. Thus, it can be easily checked whether or not the resonant frequency f& is stable. For correction of the resonant frequency $f_r$, it may be, as in correction of the application frequency $f_b$, optionally selected whether correction is automatically or manually performed.

Third Example

Figure 14:
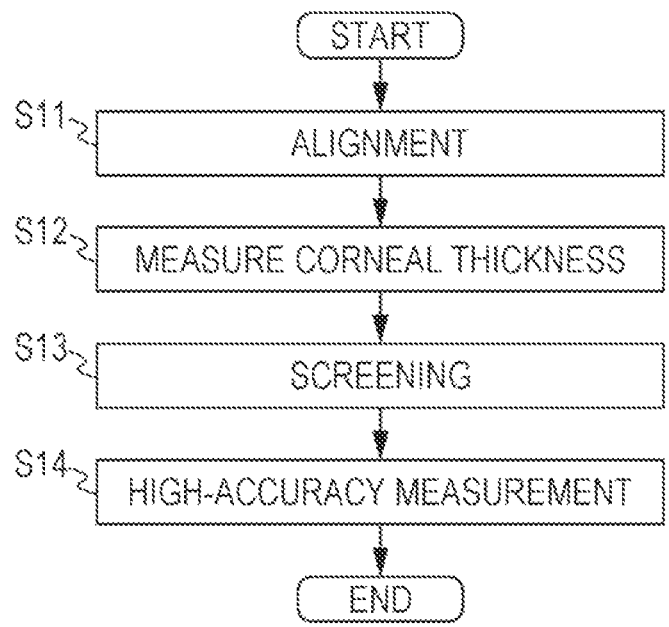
FIG. 14 is a flowchart of control operation.

A third example will be described. An ultrasonic tonometer of the third example performs control operation as described below (see FIG. 14). A mechanical configuration is similar to that of the first example, and therefore, the same reference numerals are used and description thereof will be omitted.

(Step 11: Alignment)

First, a controller 70 aligns a measurer 3 with an examinee's eye. The face of an examinee is supported on a face supporter 4. For example, the controller 70 detects a raster generated by a target projector 250 from an anterior segment front image acquired by a light receiving element 222. The controller 70 drives a driver 5 such that the position of the raster reaches a predetermined position. Needless to say, while viewing a display 75, an examiner may manually perform alignment with the examinee's eye by means of, e.g., an operator 76. After having driven the driver 5, the controller 70 determines alignment appropriateness based on whether or not the position of the raster of the anterior segment image is at the predetermined position.

(Step S12: Corneal Thickness Measurement)

After completion of alignment with the examinee's eye E, the controller 70 measures a corneal thickness by a corneal thickness measurement system 270. For example, the controller 70 calculates the corneal thickness based on a light receiving signal received by a light receiving element 275. For example, the controller 70 may obtain, based on the light receiving signal, the corneal thickness from a position relationship between a peak value obtained by light reflected on a corneal anterior surface and a peak value obtained by light reflected on a corneal posterior surface. The controller 70 causes, e.g., a storage 74 to store the obtained corneal thickness, for example.

(Step S13: Screening)

Figure 15A:
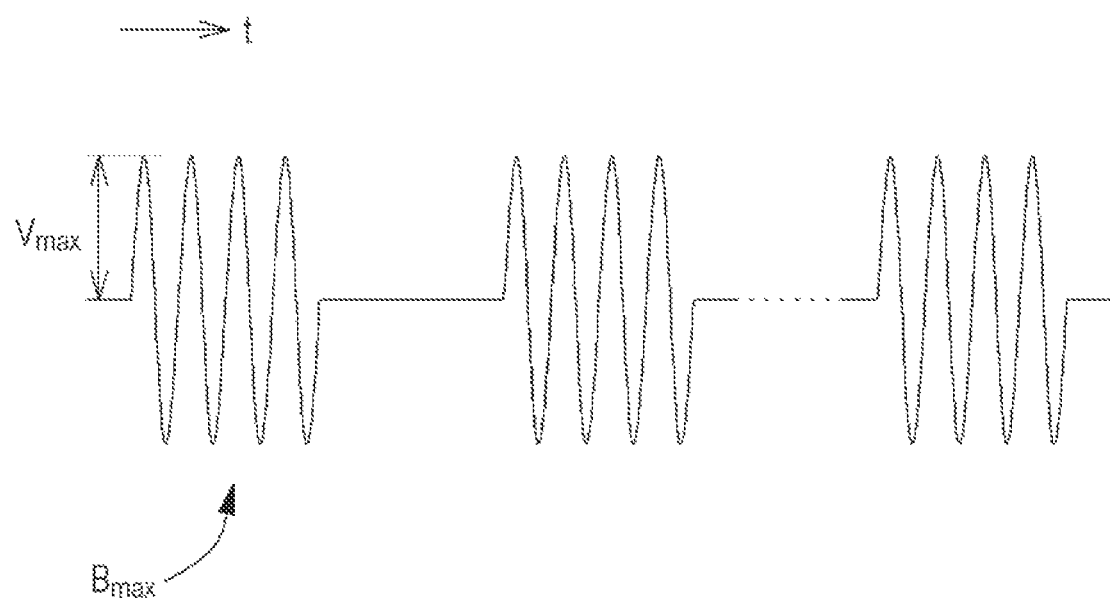
FIG. 15A is a graph of the waveform of a voltage signal.

The controller 70 measures an eye pressure in a screening mode. In the screening mode, a rough eye pressure of the examinee's eye is measured in a short period of time. For example, the controller 70 applies a burst wave $B_{max}$ with the maximum voltage $V_{max}$ as illustrated in FIG. 15A to an ultrasonic element 110 of an ultrasonic actuator 100. Accordingly, the ultrasonic actuator 100 irradiates the examinee's eye with an ultrasonic wave. The cornea of the examinee's eye is deformed by an acoustic radiation pressure generated by the ultrasonic wave. The controller 70 detects, based on a cornea deformation signal (a light receiving signal of a light receiving element 263) obtained by a deformation detection system 260, that the cornea has deformed to a predetermined shape (an applanation or flat state).

The controller 70 calculates, for example, the eye pressure of the examinee's eye based on the acoustic radiation pressure when the cornea of the examinee's eye deforms to the predetermined shape. The acoustic radiation pressure applied to the examinee's eye is associated with ultrasonic wave irradiation time, and increases as the ultrasonic wave irradiation time increases. Thus, the controller 70 obtains the acoustic radiation pressure based on the ultrasonic wave irradiation time. A relationship between the acoustic radiation pressure when the cornea deforms to the predetermined shape and the eye pressure of the examinee's eye is obtained in advance by, e.g., experiment, and is stored in, e.g., a storage 74. The controller 70 determines an eye pressure value of the examinee's eye based on the acoustic radiation pressure when the cornea deforms to the predetermined shape and the relationship stored in the storage 74.

(Step S14: High-Accuracy Measurement)

Figure 15B:
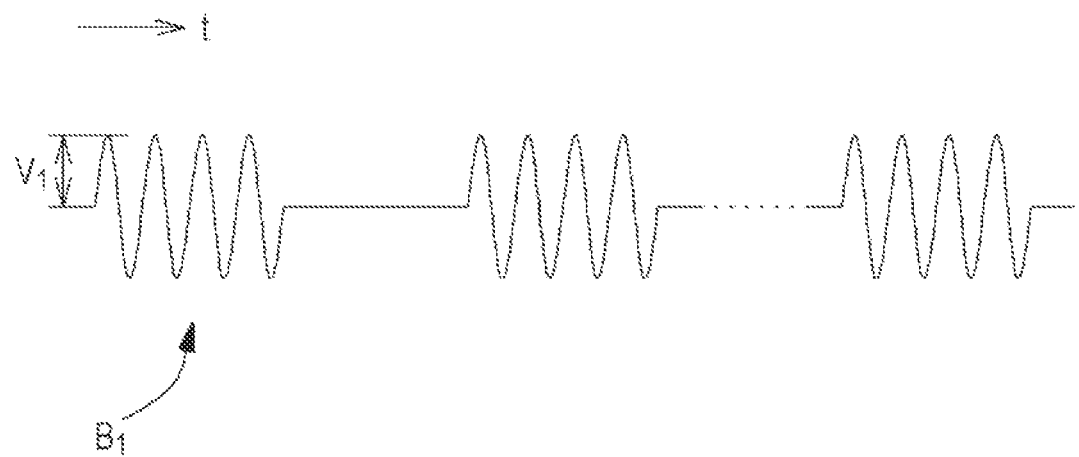
FIG. 15B is a graph of the waveform of a voltage signal.
Figure 16A:
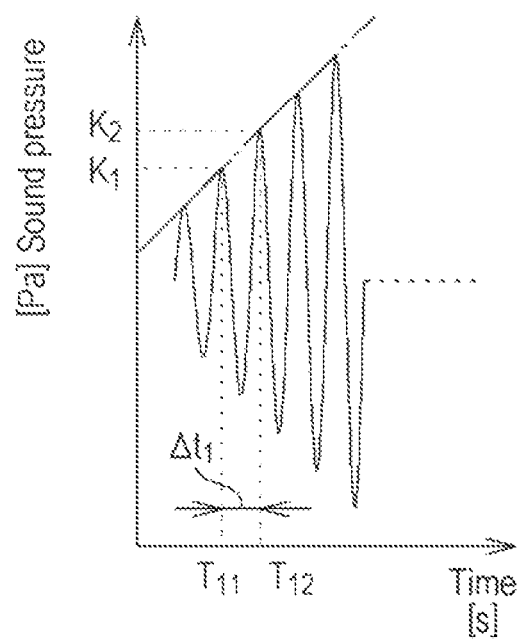
FIG. 16A is a graph of a temporal change in a sound pressure level of an ultrasonic wave.
Figure 16B:
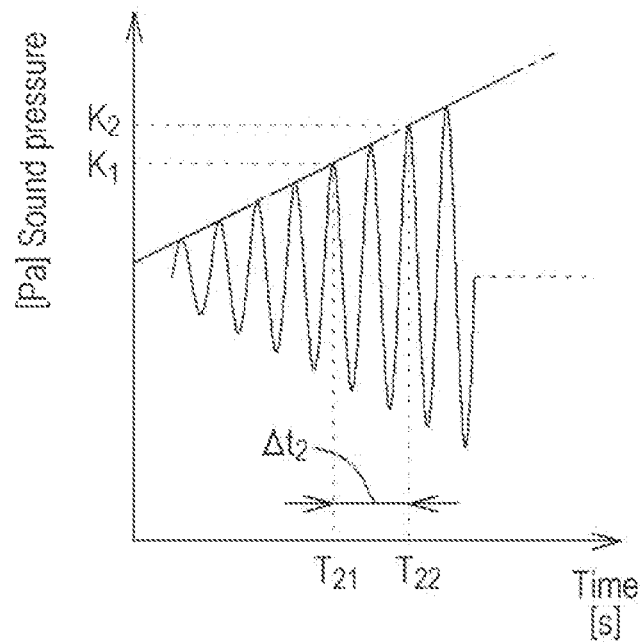
FIG. 16B is a graph of a temporal change in a sound pressure level of an ultrasonic wave.

Subsequently, the controller 70 measures the eye pressure in a high-accuracy measurement mode. In the high-accuracy measurement mode, the eye pressure is measured with higher accuracy than that in the screening mode. The controller 70 controls a voltage applied to the ultrasonic element 110, thereby changing the rate of increase in a sound pressure (e.g., the amount of increase per unit time) and improving measurement accuracy. For example, the controller 70 applies the burst wave $B_{max}$ with the maximum voltage $V_{max}$ as illustrated in FIG. 15A in the screening mode, whereas applies a burst wave $B_1$ with a lower voltage Vi than the maximum voltage $V_{max}$ as illustrated in FIG. 15B to the ultrasonic element 110. The controller 70 decreases the voltage applied to the ultrasonic element 110, thereby slowing an increase in the sound pressure. For example, FIG. 16A is a graph of a temporal change in the sound pressure when the voltage with the burst wave $B_{max}$ is applied, and FIG. 16B is a graph of a temporal change in the sound pressure when the voltage with the burst wave $B_1$ is applied. As illustrated in FIGS. 16A and 16B, the rate of increase in the sound pressure to time is lower in the case of applying a lower voltage than in the case of applying a higher voltage.

Figure 17A:
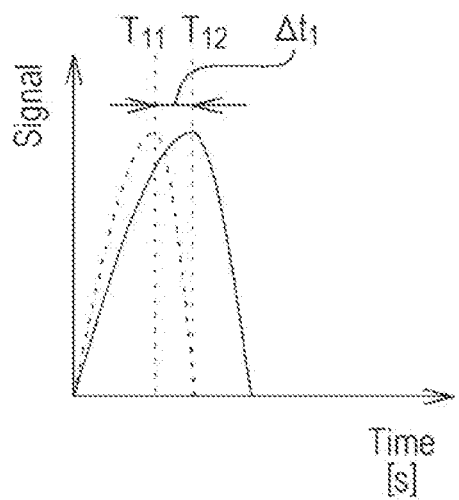
FIG. 17A is a graph of a temporal change in a cornea deformation signal.
Figure 17B:
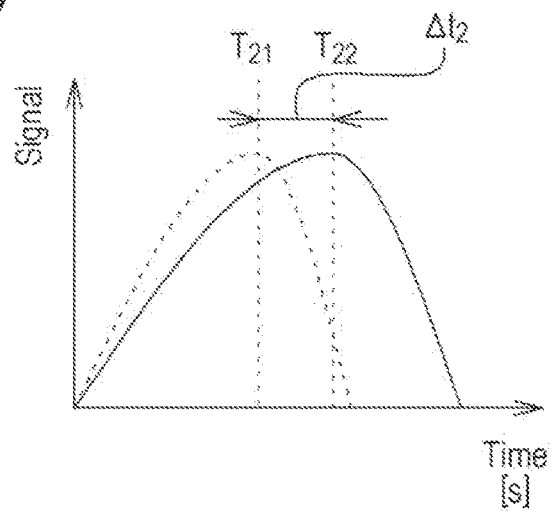
FIG. 17B is a graph of a temporal change in a cornea deformation signal.

For example, it is assumed that a sound pressure required for measurement for an examinee's eye with an eye pressure value $P_a$ is $K_1$ and a sound pressure required for measurement for an eye pressure value $P_b$ ($>P_a$) greater than the eye pressure value $P_a$ is $K_2$. Moreover, as illustrated in FIGS. 16A and 16B, it is assumed that time until the sound pressure $K_1$ after the burst wave $B_{max}$ has been applied is $T_{11}$ and time until the sound pressure $K_2$ after the burst wave $B_{max}$ has been applied is $T_{12}$. Further, it is assumed that time until the sound pressure $K_1$ after the burst wave $B_1$ has been applied is $T_{21}$ and time until the sound pressure $K_2$ after the burst wave $B_1$ has been applied is $T_{22}$. By decreasing the voltage, an increase in the sound pressure is slowed. Thus, an interval $\Delta t_2$ between the time $T_{21}$ and the time $T_{22}$ is longer than an interval $\Delta t_1$ between the time $T_{11}$ and the time $T_{12}$. Thus, a temporal resolution is improved. For example, FIG. 17A illustrates a cornea deformation signal when the burst wave $B_{max}$ is applied, and FIG. 17B illustrates a cornea deformation signal when the burst wave $B_1$ is applied. Moreover, in FIGS. 17A and 17B, thick dashed lines indicate cornea deformation signals when measurement is performed for the eye with the eye pressure value $P_a$, and solid lines indicate cornea deformation signals when measurement is performed for the eye with the eye pressure value $P_b$. By slowing an increase in the sound pressure, an interval between the peaks of the cornea deformation signals for each eye pressure value is expanded, and therefore, the probability of erroneous detection of a peak position is decreased. Thus, eye pressure measurement accuracy is improved.

Figure 18A:
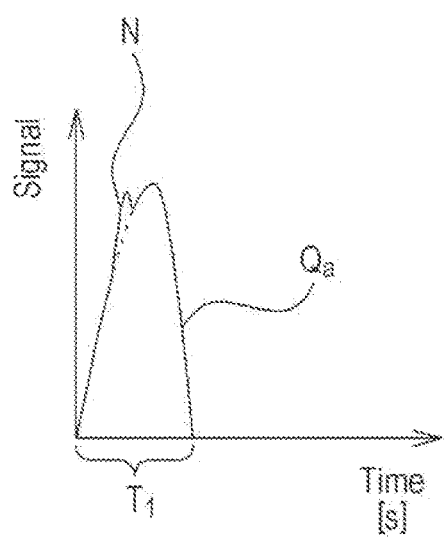
FIG. 18A is a graph of a temporal change in a cornea deformation signal when noise is caused.
Figure 18B:
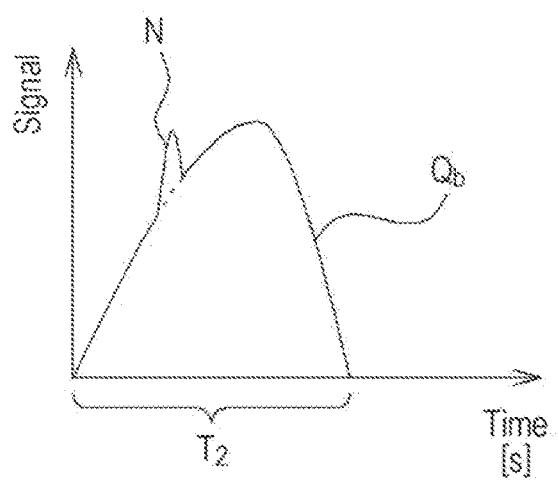
FIG. 18B is a graph of a temporal change in a cornea deformation signal when noise is caused.

FIG. 18A illustrates a cornea deformation signal $Q_a$ when the burst wave $B_{max}$ is applied, and FIG. 18B illustrates a cornea deformation signal $Q_b$ when the burst wave $B_1$ is applied. The cornea deformation signals $Q_a$, $Q_b$ as described herein are signals upon measurement for eyes with the same eye pressure. Detection time $T_2$ for the cornea deformation signal $Q_b$ is longer than detection time $T_1$ for the cornea deformation signal $Q_a$, and a change in the cornea deformation signal is slow. Thus, even in a case where unexpected noise (peak noise) N has been caused, it is less likely to erroneously detect the peak of the cornea deformation signal.

The controller 70 applies the voltage Vi to the ultrasonic element 110, thereby deforming the examinee's eye by the acoustic radiation pressure more slowly increasing as compared to the screening mode. Then, the controller 70 detects, by the deformation detection system 260, that the cornea has deformed to the predetermined shape, and based on the level of the acoustic radiation pressure thereupon, measures the eye pressure of the examinee's eye.

As described above, the ultrasonic tonometer of the third example controls the sound pressure or acoustic radiation pressure of the ultrasonic wave so that the eye pressure measurement accuracy can be changed. Thus, the eye pressure can be simply measured in a short period of time, and can be measured with high accuracy. Consequently, measurement can be performed in association with the intended use of the device.

Note that in the above-described third example, the rate of increase in the sound pressure or the acoustic radiation pressure is controlled in such a manner that the voltage applied to the ultrasonic element 110 is controlled, but the present disclosure is not limited to such a configuration. For example, the rate of increase in the sound pressure or the acoustic radiation pressure may be adjusted in such a manner that a current applied to the ultrasonic element 110 is controlled, and accordingly, the eye pressure measurement accuracy may be changed. For example, the current flowing in the ultrasonic element 110 in the high-accuracy measurement mode may be decreased as compared to the screening mode, and in this manner, the rate of increase in the sound pressure may be decreased and the measurement accuracy may be increased. Alternatively, the rate of increase in the sound pressure or the acoustic radiation pressure may be adjusted in such a manner that the frequency of the voltage applied to the ultrasonic element 110 is controlled.

Note that the controller 70 may perform switching to the high-accuracy measurement mode based on the eye pressure value measured in the screening mode. For example, in the case of a great eye pressure value, if measurement in the high-accuracy measurement mode is performed, there is a probability that it takes time to complete measurement and a burden is on the examinee. For this reason, in a case where the eye pressure value measured in the screening mode is equal to or less than a predetermined value, switching to the high-accuracy measurement mode may be performed.

Alternatively, based on the eye pressure value measured in the screening mode, the sound pressure or the acoustic radiation pressure in the high-accuracy measurement mode may be controlled. For example, as the eye pressure value in the screening mode decreases, the rate of increase in the sound pressure in the high-accuracy measurement mode may decrease. With this configuration, eye pressure measurement can be performed for an examinee with a smaller eye pressure value with more favorable accuracy, and an increase in measurement time for an examinee with a great eye pressure value can be avoided.

Note that in the case of performing measurement in multiple measurement modes with different levels of accuracy, all measurement results are not necessarily displayed on the display 75. For example, the measurement result obtained in any one of the measurement modes may be displayed on the display 75. For example, the measurement result obtained in a higher-accuracy measurement mode of the multiple measurement modes may be displayed on the display 75.

Note that the method for calculating the eye pressure is not limited to above, and various methods may be used. For example, the controller 70 may obtain the eye pressure in such a manner that the amount of deformation of the cornea is obtained by the deformation detection system 260 and is multiplied by a conversion factor. Note that the controller 70 may correct the calculated eye pressure value according to the corneal thickness stored in the storage 74, for example.

Note that the controller 70 may measure the eye pressure based on the ultrasonic wave reflected on the examinee's eye. For example, the eye pressure may be measured based on a change in the characteristics of the ultrasonic wave reflected on the examinee's eye. Alternatively, the controller 70 may acquire the amount of deformation of the cornea from the ultrasonic wave reflected on the examinee's eye, and based on such a deformation amount, may measure the eye pressure. Alternatively, the eye pressure may be obtained based on vibration characteristics of the cornea upon irradiation with the ultrasonic wave.

LIST OF REFERENCE SIGNS

1 non-contact ultrasonic tonometer
2 base
3 housing
4 face supporter
6 support base
100 ultrasonic actuator
200 optical unit
400 attachment portion
500 detector

The invention claimed is:

1. An ultrasonic tonometer for measuring an eye pressure of an examinee's eye by means of an ultrasonic wave, comprising:
   an ultrasonic actuator having an ultrasonic element and configured to irradiate the examinee's eye with the ultrasonic wave;
   current adjustment means including a variable inductor capable of changing an impedance;
   control means configured to control the current adjustment means to change the impedance of the variable inductor to adjust a current applied to the ultrasonic element to control a sound pressure or acoustic radiation pressure of the ultrasonic wave; and
   acquisition means configured to acquire current information regarding a level of a current flowing in the ultrasonic actuator,
   wherein the control means controls the current adjustment means based on the current information,
   the variable inductor comprises a core and a coil, and
   the control means is configured to change the position of the core relative to the coil to change the impedance of the variable inductor.

2. The ultrasonic tonometer according to claim 1, wherein the control means controls the current adjustment means such that a predetermined current flows in the ultrasonic actuator.

3. The ultrasonic tonometer according to claim 1, wherein the acquisition means acquires the current information by detecting output of the ultrasonic actuator.

4. The ultrasonic tonometer according to claim 1, wherein the acquisition means acquires the current information by detecting a value of current or voltage applied to the ultrasonic element or a resistance value of the ultrasonic element.

* * * * *